(12) United States Patent
Hargreaves et al.

(10) Patent No.: US 6,219,571 B1
(45) Date of Patent: Apr. 17, 2001

(54) MAGNETIC RESONANCE IMAGING USING DRIVEN EQUILIBRIUM FOURIER TRANSFORM

(75) Inventors: Brian A. Hargreaves, Stanford; Dwight G. Nishimura, Palo Alto, both of CA (US)

(73) Assignee: Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/280,223

(22) Filed: Mar. 29, 1999

Related U.S. Application Data
(60) Provisional application No. 60/080,904, filed on Apr. 6, 1998.

(51) Int. Cl.[7] ................................................ A61B 5/055
(52) U.S. Cl. .......................... 600/410; 324/307; 324/309
(58) Field of Search ............................ 600/410; 324/307, 324/309

(56) References Cited

U.S. PATENT DOCUMENTS

| | | | |
|---|---|---|---|
| 4,165,479 | * 8/1979 | Mansfield | 324/309 |
| 4,509,015 | 4/1985 | Ordidge et al. | 324/309 |
| 4,532,474 | 7/1985 | Edelstein | 324/309 |
| 4,665,365 | 5/1987 | Glover et al. | 324/309 |
| 4,766,381 | * 8/1988 | Conturo et al. | 324/309 |
| 4,893,081 | 1/1990 | Zur | 324/309 |
| 5,245,282 | * 9/1993 | Mugler, III et al. | 324/309 |
| 5,303,705 | * 4/1994 | Nenov | 600/410 |

OTHER PUBLICATIONS

Shoup, R.R. et al., "The Driven Equilibrium Fourier Transform NMR Technique: An Experimental Study," *Journal of Magnetic Resonance* 8, 298–310 (1972).

Iwaoka, Hideto et al., "A New Pulse Sequence for "Fast Recovery" Fast–Scan NMR Imaging," *IEEE Transactions on Medical Imaging*, vol. MI–3, No. 1, pp. 41–46, Mar. 1984.

Van Uijen, C.M.J. et al., "Driven–Equilibrium Radiofrequency Pulses in NMR Imaging," *Magnetic Resonance in Medicine I,* 502–507 (1984).

(List continued on next page.)

*Primary Examiner*—Brian L. Casler
(74) *Attorney, Agent, or Firm*—Townsend and Townsend and Crew LLP; Henry K. Woodward (57) ABSTRACT

A new technique for imaging a material with a high T2/T1 ratio such as articular cartilage uses driven equilibrium Fourier transform (DEFT), a method of enhancing signal strength without waiting for full T1 recovery. Compared to other methods, DEFT imaging provides a good combination of bright cartilage and high contrast between cartilage and surrounding tissue. Both theoretical predictions and images show that DEFT is a valuable method for imaging articular cartilage when compared to spoiled gradient recalled acquisition in the steady-state (SPGR) or fast spin echo (FSE). T2-decay, T1 recovery, echo time, magnetization density, proton density, and equilibrium density per proton are related by a derived equation.

16 Claims, 8 Drawing Sheets

OTHER PUBLICATIONS

Maki, J.H. et al., "SNR Improvement in NMR Microscopy Using DEFT," *Journal of Magnetic Resonance* 80, 482–492 (1988).

Rubenstein, Joel D. et al., "Image Resolution and Signal-to-Noise Ratio Requirements for MR Imaging of Degenerative Cartilage," *AJR*:169, , pp. 1089–1096, Oct. 1997.

Yao, Lawrence et al., "MR Imaging of Joints: Analytic Optimization of GRE Techniques of 1.5 T," *AJR*:158, pp 339–343 Feb. 1992.

Brittain, Jean H. et al., "Coronary Angiography with Magnetization–Prepared $T_2$ Contrast," *MRM*, 33:689–696 (1995).

Henkelman, R.Mark et al., "Anisotropy of NMR Properties of Tissues," *MRM* 32:592–601 (1994).

Recht, Michael P. et al., "MR Imaging of Articular Cartilage: Current Status and Future Directions," *AJR*:163–283–290 (1994).

Peterfy, Charles G., et al., "MR Imaging of the Arthritic Knee: Improved Discrimination of Cartilage, Synovium, and Effusion with Pulsed Saturation Transfer and Fat-suppressed T1–weighted Sequences," *Radiology* 191:413–419 (1994).

* cited by examiner

MAGNETIC RESONANCE IMAGING USING DRIVEN EQUILIBRIUM FOURIER TRANSFORM

This application is a continuation of and claims the benefit of U.S. Provisional Application No. 60/080,904 filed Apr. 6, 1998, the disclosure of which is incorporated by reference.

The U.S. government has rights in the disclosed invention pursuant to NIH Contract No. HL 56394 and No. CA 509418 with Stanford University, assignee.

This invention relates generally to magnetic resonance imaging (MRI), and more particularly the invention relates to the use of driven equilibrium Fourier transform (DEFT) for musculoskeletal imaging.

BACKGROUND OF THE INVENTION

The background will be described with reference to prior art publications listed in the attached appendix.

Magnetic resonance (MR) imaging is the most accurate non-invasive test for assessing tears of the menisci and the cruciate ligaments of the knee (1,2). MR imaging of the knee has replaced conventional arthrography in evaluating meniscal and ligamentous disorders and has decreased the morbidity and the cost associated with negative arthroscopy (3,4). Additionally, much progress has been made in recent years in imaging articular cartilage (5,6). However, there is still a lot of disagreement on which pulse sequences are best suited for imaging articular cartilage. Current sequences are often limited by insufficient spatial resolution and inadequate signal-to-noise ratio (SNR) (7).

In magnetic resonance (MR) imaging, the scan sequence type and scan parameters are chosen prior to the scan. The choice of sequence and parameters depends on the desired image signal-to-noise ratio (SNR) and contrast-to-noise (CNR). The signal level and contrast can be determined from a signal equation for the sequence which relates signal level to the scan parameters and the tissue parameters (T1, T2 and proton density).

The primary goal of cartilage imaging is to accurately depict cartilage structure and abnormalities, which requires high resolution and high SNR. The tissue characteristics of cartilage, specifically its short T2 and low proton density, make this challenging. The amount of joint fluid is often increased with patients with cartilage damage or other articular disorders. In this instance, joint fluid can fill cartilage and tears as well as meniscal tears. Thus a high image contrast-to-noise ratio (CNR) between joint fluid and other tissue can be very useful for diagnoses of cartilage or injuries or meniscal tears, as has already been shown clinically using saline MR arthrography (8,9). However, MR arthrography is invasive, so that there is much demand for non-invasive imaging methods. A useful method of imaging cartilage would show joint fluid brightly while also preserving cartilage signal, thus allowing visualization of both the cartilage surface and substance.

There are currently many popular methods used in knee imaging and cartilage imaging. Recht and Resnick (10) provide a good overview of these methods. Many groups (5,11) have found that spoiled gradient recalled echo imaging provides very desirable contrast characteristics. An analytical parameter optimization for gradient recalled echo (GRE) including spoiled gradient-recalled acquisition in the steady state (SPGR) techniques is given in (12). A comparison of 3D SPGR with "standard" methods including T1- and T2-weighted SE, gradient-recalled acquisition in the steady state (GRASS), and 2D SPGR is presented in (13).

Fast spin echo (FSE) imaging has become very popular owing to its high scan-time efficiency. FSE imaging allows for proton density (PD) weighted images and T2-weighted images, both of which can provide good contrast between cartilage and joint fluid (14). Contrast-enhanced techniques are also being used in knee imaging. Gd-DPTA$^2$—imaging (15,16) and sodium imaging (17) are methods which image the proteoglycan content in the cartilage, which is thought to be early sign of degenerative cartilage. Other methods which are useful in knee imaging include magnetization transfer contrast (MTC) (6,18), dual-echo in the steady state (DESS) (19), and diffusion-weighted imaging (20).

Driven equilibrium Fourier transform (DEFT) imaging has been used in the past as a method of signal enhancement (21–25). Because this signal enhancement depends on the tissue T1 and T2 it has been discovered in accordance with the present invention that DEFT can be used to generate tissue contrast while maintaining a high signal to noise ratio. Frequently, a choice has to be made between SNR and CNR. By attenuating the signal of one tissue, the CNR can be increased, but the SNR for that tissue drops. However, DEFT imaging tends to simultaneously achieve high SNR and CNR. Some tissues, particularly those with short T2 and long T1 are difficult to image with a high SNR. With DEFT imaging, these tissues are often seen as brightly or more brightly than with other sequences. The DEFT signal enhancement is greatest for tissues in which the T2 is a reasonably high fraction of T1. The end result is that both tissues have a good SNR, and there is strong contrast between the tissues.

In one application, DEFT generates contrast between cartilage and joint fluid by enhancing the signal from joint fluid, rather than by suppressing the cartilage signal like some sequences do.

SUMMARY OF THE INVENTION

In accordance with the invention, DEFT imaging is employed to realize a CNR while maintaining a high SNR. An example application of the invention is with cartilage imaging. Cartilage is often surrounded by synovial fluid, which has a high T2/T1 ratio. The short T2 of cartilage makes imaging difficult, but the use of DEFT in accordance with the invention achieves a good SNR with the synovial fluid being bright.

Clinically, T1 and T2 contrast images are used for medical diagnoses. In T1-weighted scans, the faster recovery of the shorter-T1 tissue causes its signal to be brighter than that of the longer-T1 tissue. In T2-weighted scans, the slower decay of the longer-T2 tissue causes it to be brighter. In accordance with the present invention, a DEFT imaging sequence is employed for increasing brightness with the ratio T2/T1 of material in an imaged region.

The relationship of echo-train lengths, various flip angles, and different types of flip angles is established by a signal equation derived from the signal equation for DEFT imaging. The signal equation is used to compare the contrast and SNR efficiency of DEFT imaging to other sequences.

The invention and objects and features thereof will be more readily apparent from the following description and appended claims when taken with the drawings.

DETAILED DESCRIPTION OF THE SPECIFIC EMBODIMENTS

Figure 10A:
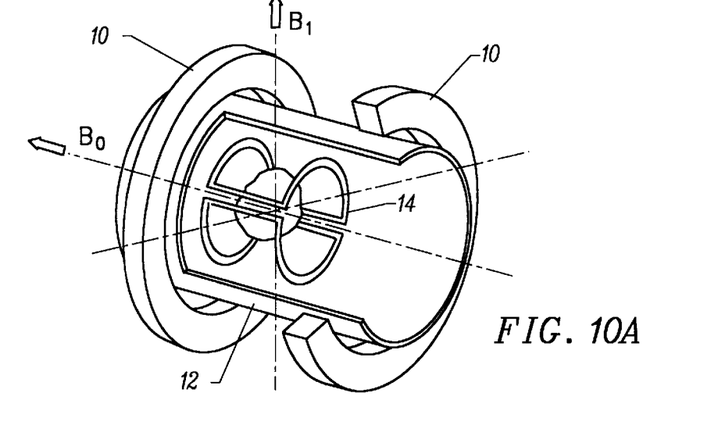
FIGS. 10a–10d illustrate the arrangement of conventional MRI apparatus and magnetic fields generated therein.
Figure 10B:
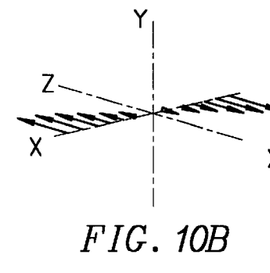
Figure 10C:
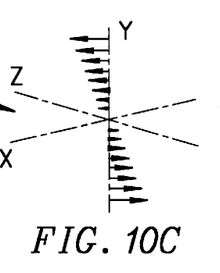
Figure 10D:
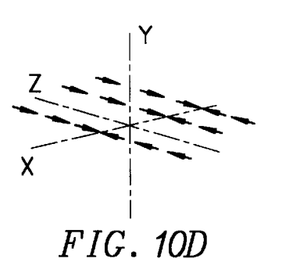

Referring now to the drawings, FIG. 10A is a perspective view partially in section illustrating coil apparatus in an NMR imaging system, and FIGS. 10B–10D illustrate field gradients which can be produced in the apparatus of FIG. 1A. This apparatus is discussed by Hinshaw and Lent. "An Introduction to NMR Imaging: From the Bloch Equation to the Imaging Equation." *Proceedings of the IEEE*, Vol. 71, No. 3, March 1983, pp. 338–350. Briefly, the uniform static field B0 is generated by the magnet comprising the coil pair 10. A gradient field $G_x$ is generated by a complex gradient coil set which can be wound on the cylinder 12. An RF field B 1 is generated by a saddle coil 14. A patent undergoing imaging would be positioned along the Z axis within the saddle coil 14.

In FIG. 10B an X gradient field is shown which is parallel to the static field B0 and varies linearly with distance along the X axis but does not vary with distance along the Y and Z axes. FIGS. 10C and 10D are similar representation of the Y gradient and Z gradient fields, respectively.

Figure 11:
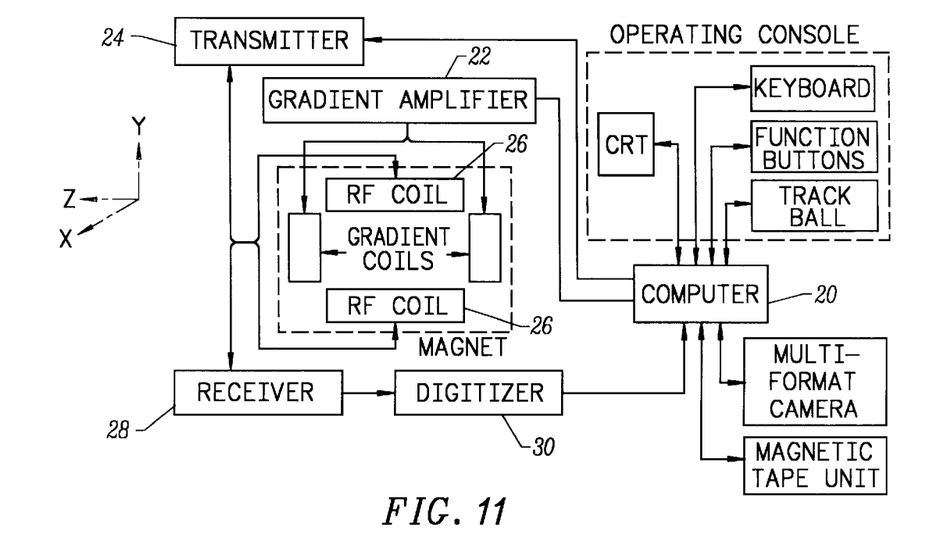
FIG. 11 is a functional block diagram of MRI imaging.

FIG. 11 is a functional block diagram of the imaging apparatus as disclosed in NMR—*A Perspective on Imaging*, General Electric Company. A computer 20 is programmed to control the operation of the NMR apparatus and process free induction decay (FID) signals detected therefrom. The gradient field is energized by a gradient amplifier 22 and the RF coils for impressing an RF magnetic moment at the Larmor frequency is controlled by the transmitter 24 and the RF coils 26. After the selected nuclei have been flipped, the RF coils 26 are employed to detect the FID signal which is passed to the receiver 28 and thence through digitizer 30 for processing by computer 20.

In accordance with the present invention, a DEFT imaging sequence is employed for increasing brightness with the ratio T2/T1 of material in an imaged region.

Figure 1:
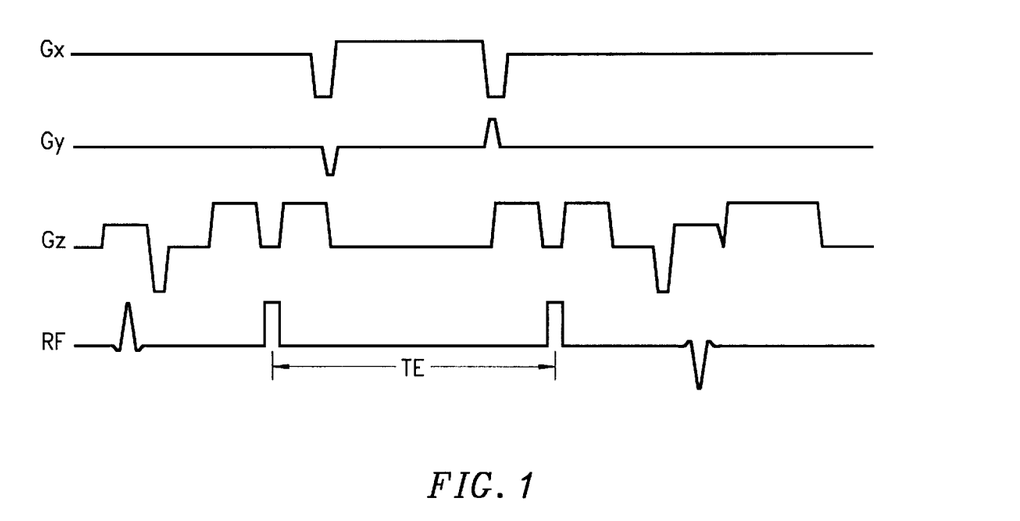
FIG. 1 illustrates a DEFT pulse sequence.

The DEFT pulse sequence, first proposed by Becker and Ferretti (21), is shown in FIG. 1. A slice-selective RF excitation pulse tips the magnetization through an angle of a about the x-axis. Two $180°_y$ refocusing pulses result in two spin echoes. The first spin echo is used for imaging, using a 2DFT k-space trajectory, which returns to the k-space origin after each readout. At the second spin echo, a $-α_x$ "driven equilibrium" pulse (or tip-up pulse) tips remaining magnetization back to the longitudinal axis. The $-α_x$ is surrounded by a time-reversed slice-select gradient. A gradient pulse at the end of the sequence helps to spoil residual transverse magnetization.

The flip angle, α, can be modified, with similar results to gradient-echo imaging. As with gradient echo imaging, there is a flip angle which maximizes the DEFT signal for a particular tissue. For cartilage, and TR>200 ms, the optimal flip angle varies from around 43° to 90°. However, in this range TR, the signal at the optimal flip angle is within 10% of the signal at a flip angle of 90°. Herein, a 90° flip angle has been used in all cases.

The non-selective refocusing pulses can be replaced with composite pulses as described in (26). The composite $90°_x$–$180°_y$–$90°_x$ combination which results in a $180°_y$ tip which is much less sensitive to variations in $B_0$ and $B_1$. The composite pulses can be used with the single-slice sequence, but are not useful in multi-slice imaging because the pulse duration becomes too large.

In imaging of cartilage, we have found a fat-presaturation pulse to be useful. This suppresses the fatty bone marrow, which otherwise significantly reduces the dynamic range of the cartilage in the image. The fat-presaturation pulse is a spectrally selective $90°_x$ tip, followed by a transverse spoiler pulse to dephase the magnetization from fat.

In implementing DEFT, there are few complications. The sequence is quite robust to $B_0$ or $B_1$ variations, especially when composite refocusing pulses are used. DEFT is sensitive to refocusing errors prior to the tip-up pulse, and thus requires accurate pulse timing, especially in off-isocenter imaging. We have repeatedly seen significant signal attenuation during development stages due to this sensitivity, and have solved the problem by verifying that the pulse timing is perfect.

Figure 2:
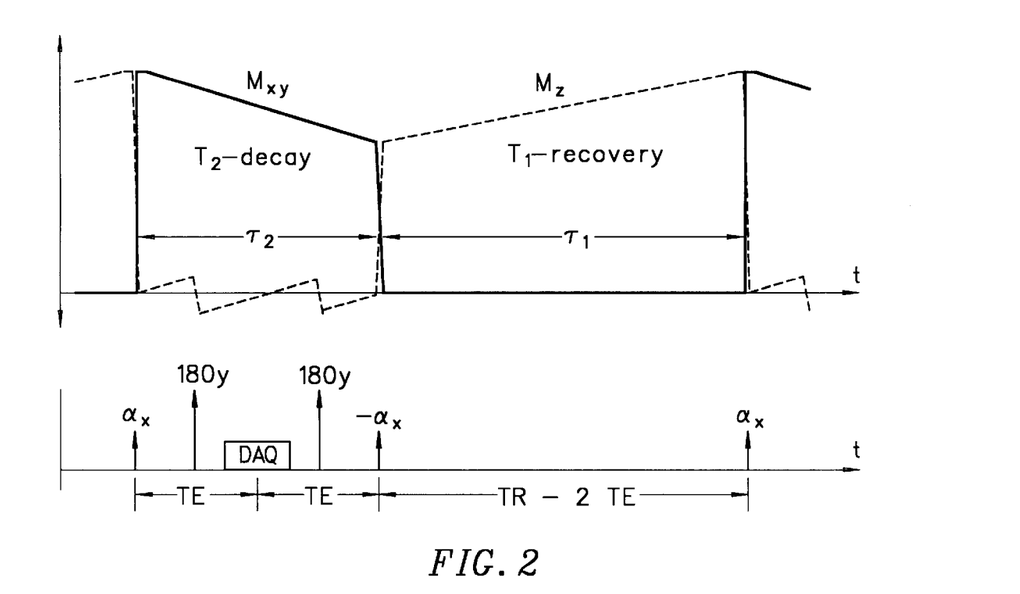
FIG. 2 illustrates steady-state magnetizations in a DEFT sequence.

The signal level of a DEFT sequence can be calculated by dividing the DEFT sequence into two parts. In the first part, the magnetization is in the transverse plane. It is assumed that because of the spin echoes, the longitudinal recovery is negligible. In the second part of the sequence, the magnetization is primarily along the longitudinal axis. One can neglect any remaining transverse magnetization, both because it decays and because it is dephased. The two parts of a DEFT sequence are shown in FIG. 2.

The equilibrium magnetization density along the longitudinal axis is $$M_0 = pC \tag{1}$$

where ρ is the proton density and C is the equilibrium magnetization per proton. We use C so that signal levels can be expressed with an explicit dependence on the proton density, ρ. Assume a steady-state magnetization of $M_{ss}$ along the longitudinal axis prior to the tip-down pulse. In the first part of the sequence, T2 decay causes the magnetization to decay to a level of $$M'_{ss} = M_{ss} e^{\frac{T2}{T_2}}$$

(see top of, where T2 is the duration for which the magnetization is in the transverse plane.

In the second part of the sequence, T1 recovery results in $$M_{ss} = M_0\left(1 - e^{-\frac{\tau_1}{T_1}}\right) + M'_{ss} e^{-\frac{\tau_1}{T_1}}$$

where T1 is the recovery time.

In the steady state, these parts balance, which yields, using Eq. [1]

$$M_{ss} = \rho C \frac{1 - e^{-\frac{\tau_1}{T_1}}}{1 - e^{-\frac{\tau_2}{T_2}} e^{-\frac{\tau_1}{T_1}}} \quad (2)$$

Assuming that $T2 \ll T_2$ and $\tau_1 \ll T_1$ Eq. [2] reduces to $$M_{ss} \approx \frac{\rho C}{1 + \frac{T_2}{T_2}\frac{\tau_2}{\tau_1}} \quad (3)$$

The measured signal is proportional to the magnetization density, $M_0$, which in turn is proportional to the proton density, $\rho$. Assuming that the time from tip-down to the center of the readout is TE, the measured signal is $$S \propto M_{ss} e^{-\frac{TE}{T_2}} \quad (4)$$

Note that in many cases, when Eq. [3] is valid, the factor $$e - \frac{TE}{T_2}$$

can be ignored, so that $$S \approx k \frac{\rho C}{1 + \frac{T_1}{T_2}\frac{\tau_2}{\tau_1}} \quad (5)$$

where k is the constant of proportionality, and S if the measured signal.

Although a similar derivation of Eq. [5] is given by Van Uijen et al. (24), it should be noted that this approximation is accurate over a wider range of parameters than they suggest. In fact, for $T2<T2$ and $T1<T1$, the difference between the exact signal (see below) and the approximation (Eq. [5]) is less than 12%. The exact signal can be calculated by repeating the entire analysis, taking into account both longitudinal and transverse magnetization during the entire sequence.

Equation [5] is extremely useful for analyzing the DEFT sequence. First, it is clear that the signal level is an increasing function of the ratio T2/T1. Second, note the identical dependence on the ratio T1/T2.

In DEFT sequences, the minimum value of TE (or T2) is limited by the duration of spin echo pulses, and also by the duration of the readout. Because cartilage imaging is SNR-limited, the minimum readout duration is limited by SNR, rather than hardware gradient limits. The minimum TR is then limited by the desired signal; if TR is too short, the signal levels will be too low, due to saturation. The TR must be small enough to give both a reasonable scan time and good tissue contrast. The TE should be chosen as small as possible given the desired readout duration. Then the contrast should be set by varying TR. Keeping TE as small as possible will minimize the scan time for a given contrast and readout duration.

The tissues surrounding articular cartilage include bone, bone marrow, and synovial fluid. Bone has a very low proton density and a very short T2. Thus bone naturally appears dark on almost all MR images. Bone marrow is a lipid tissue, and can be suppressed using fat suppression, as has been done with FSE and GRE sequences. Synovial fluid is high in proton density, and has a long T1 and T2.

To compare sequences analytically, it is necessary to know the tissue parameters (T1, T2 and $\rho$) of cartilage and synovial fluid. Parameters for cartilage and synovial fluid have previously been measured by several groups (12, 19, 27, 28). The values we use are shown in Table 1.

TABLE 1

Tissue Parameters of Cartilage and Synovial Fluid, based on (12, 19,27, 28).

| Quantity | Cartilage | Synovial Fluid |
|---|---|---|
| T1 | 800 | 2500 |
| T2 | 40 | 800 |
| $\frac{T1}{T2}$ | 25 | 3.1 |
| $\rho$ (Rel.) | 0.7 | 1.0 |

The present invention can accurately depict cartilage using a technique with high SNR for cartilage, and good contrast between cartilage and surrounding structures. Cartilage-bone contrast occurs naturally for most sequences, since bone has both a very low proton density and a short T2. Fat suppression is used to provide contrast between cartilage and bone marrow. Finally, cartilage-fluid contrast is achievable using most of the currently used methods.

Many physical characteristics can affect tissue contrast, including $\rho$, T1, T2, chemical shift, magnetization transfer and diffusion. Here, we concentrate on $\rho$, T1 and T2. Knowing that joint fluid has a higher $\rho$ than cartilage, it is probably useful to use a contrast method which results in brighter fluid signal from other means as well.

Figure 3:
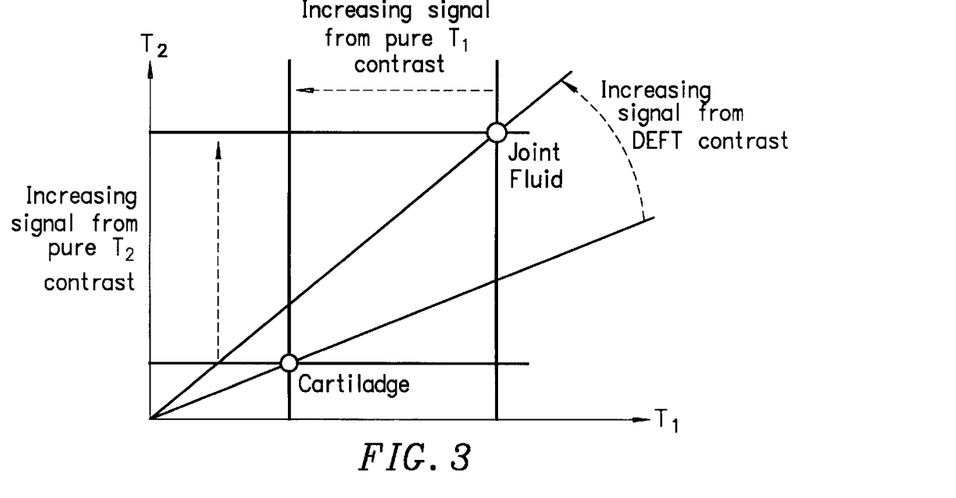
FIG. 3 illustrates contrast mechanisms of T1, T2 and DEFT contrast.

FIG. 3 shows T2 vs T1 plotted for cartilage and joint fluid. The figure shows the directions of increasing signal based on T1 and T2 differences for T1-weighted, T2-weighted, and DEFT sequences. In T1-weighted sequences, the T1 difference favors cartilage, while the $\rho$ difference favors joint fluid. Thus, contrast from T1 differences and from $\rho$ differences cancel to some extent. However, in T2-weighted or DEFT sequences, the $\rho$ difference enhances the contrast.

Many different sequences have been used to image cartilage. Here one can compare the signal levels and contrast of FSE, SPGR and DEFT sequences, taking into account the $\rho$ difference between cartilage and synovial fluid. FIG. 4 shows cartilage and fluid signals as a function of TR for T1-weighted SPGR and FSE sequences, as a function of TE for a T2-weighted spin-echo sequence, and as a function of TR for a DEFT sequence. In the T1-weighted and DEFT sequences (FIGS. 4(a), (b) and (d)), TE is kept to about the minimum achievable (TE of 8 ms for SPGR, 12 ms for FSE or DEFT) while using a 16 kHz readout bandwidth to maintain high SNR for cartilage. The SPGR and FSE sequences which we refer to as "T1-weighted" are actually $\rho$-weighted at the higher TR values.

Figure 4A:
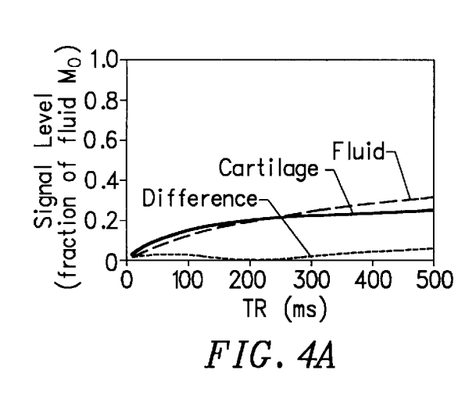
FIGS. 4a, 4b, 4c, 4d illustrates a comparison of cartilage-fluid contrast for different sequences.
Figure 4B:
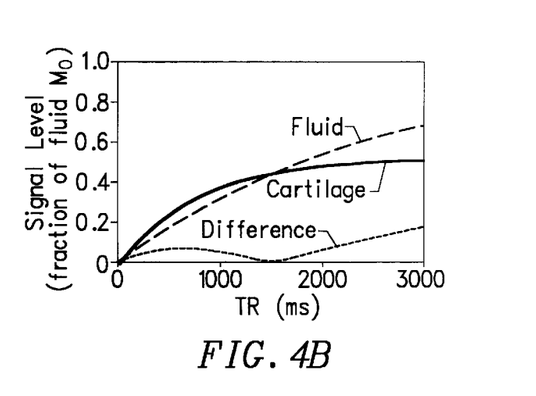

The contrast in the T1-weighted sequences sequence arises from T1 differences and $\rho$ differences. At short TR values, the effects of T1 differences and $\rho$ differences tend to cancel each other. For higher TR, the image is essentially ρ-weighted and fluid is brighter. The contrast between the tissues is not very high for any TR, because the effects of T1 differences and ρ differences compete with each other.

Figure 4C:
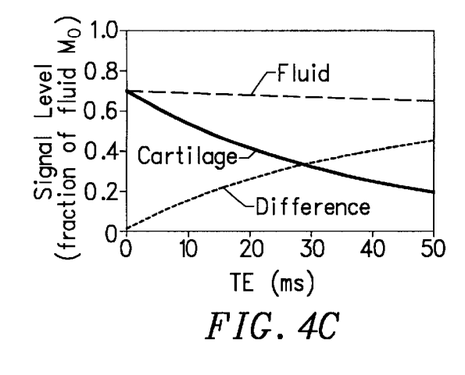

FIG. 4(c) shows the cartilage and fluid signals in a T2-weighted spin echo sequence with Tr=3000 ms. Clearly there is excellent contrast between cartilage and joint fluid, as the T2 and ρ differences both favor joint fluid.

Figure 4D:
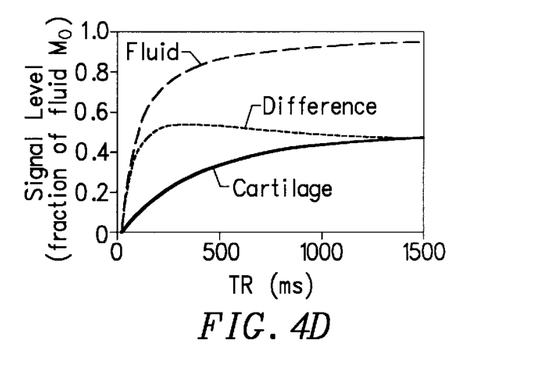

FIG. 4(d) shows the cartilage and fluid signals in a DEFT sequence. Again, there is excellent contrast between the cartilage and the joint fluid. Note, however, that the contrast is generated by enhanced fluid signal, rather than by reduced cartilage signal. The contrast on the DEFT and T2-weighted sequences is much better than on the T1-weighted SPGR and FSE sequences.

For both FSE and SPGR, signal equations have been previously calculated. The signal level on the $m^{th}$ echo for a FSE sequence (90° flip angle) with n echoes is expressed as (12)

$$S = \rho C \left(1 - e^{-\frac{TR-nTE}{T_1}}\right) e^{-\frac{mTE}{T_2}} \quad (6)$$

The signal level for a SPGR sequence is expressed as (29)

$$S = \frac{\rho C \sin\alpha \left(1 - e^{-\frac{TR}{T_1}}\right) e^{-\frac{TE}{T_2}}}{1 - e^{-\frac{TR}{T_1}} \cos\alpha} \quad (7)$$

In addition to contrast, it is important to use a sequence that has adequate SNR for cartilage. Because of the high resolution and SNR required to image cartilage structure, scan times can become very long. A good metric for the SNR performance of a sequence is relative SNR efficiency ($n_{snr}$), defined as $$\eta SNR = k \cdot \overline{signal} \sqrt{\frac{T_{acq}}{TR}} \quad (8)$$

where signal and $T_{acq}$ are the average signal level and total acquisition time over one TR.

Figure 5A:
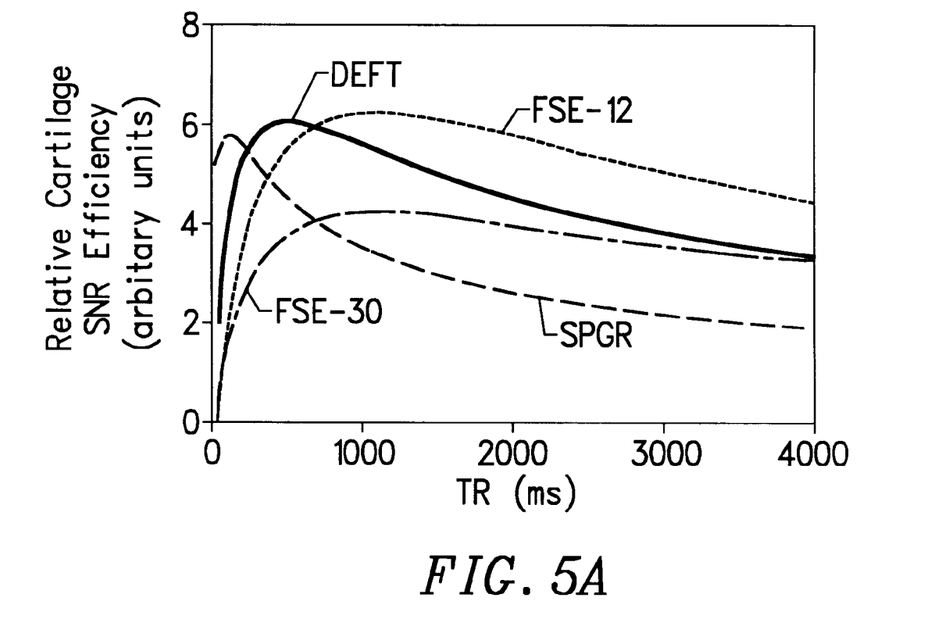
FIGS. 5a–5b illustrates a comparison of (a) Cartilage SNR efficiency and (b) Cartilage-Fluid contrast for FSE, SPGR and DEFT.
Figure 5B:
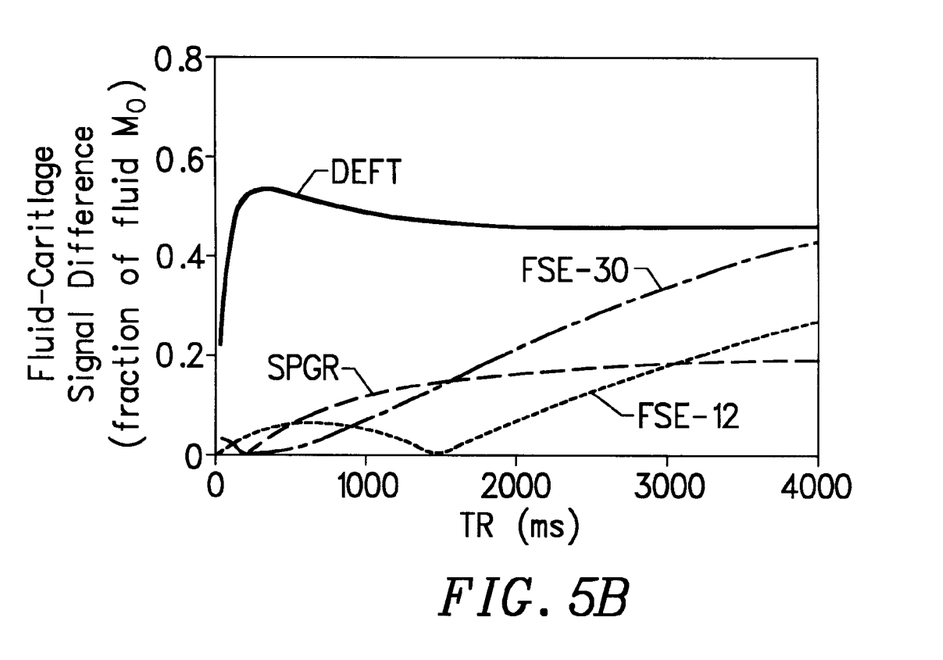

For any sequence, TR can be chosen to maximize the SNR efficiency, once the other sequence parameters including readout length and echo time have been chosen. FIG. 5(a) compares the SNR efficiency of DEFT, SPGR and FSE at different TR values. both a T1-weighted and a T2-weighted FSE sequences are used, with TE of 12 ms and 30 ms respectively. In this comparison, we assume that all sequences are single-slice. The contrast (signal difference) between cartilage and joint fluid for the same four sequences is plotted in FIG. 5(b).

Here is used an echo-train length of 4 for FSE in this comparison because it gives a higher peak SNR efficiency than an echo-train length of 8. For DEFT, a single echo, rather than multiple echo train gives the best SNR efficiency.

It is estimated that SNR efficiency for the T1-weighted FSE sequence by averaging the signal over the 4 echoes at 12 ms, 24 ms, 36 ms and 48 ms. For the T2-weighted sequence, the signal over echoes at 30 ms, 45 ms, 60 ms and 75 ms are averaged. These average signals were used in Eq. 8. The contrast calculations for the T1-weighted and T2-weighted FSE sequences use the signals from the echoes at 12 ms and 30 ms respectively.

The peak SNR efficiencies for DEFT, SPGR and T1-weighted FSE are similar, and noticeably higher than that of the T2-weighted FSE sequence. The DEFT contrast is the greatest of the four sequences, slightly greater than the contrast of the T2-weighted FSE sequence and substantially greater than the contrast of the other two sequences. It is clear from FIG. 5 that DEFT provides a better combination of cartilage SNR efficiency and tissue contrast than the other sequences.

Figure 6:
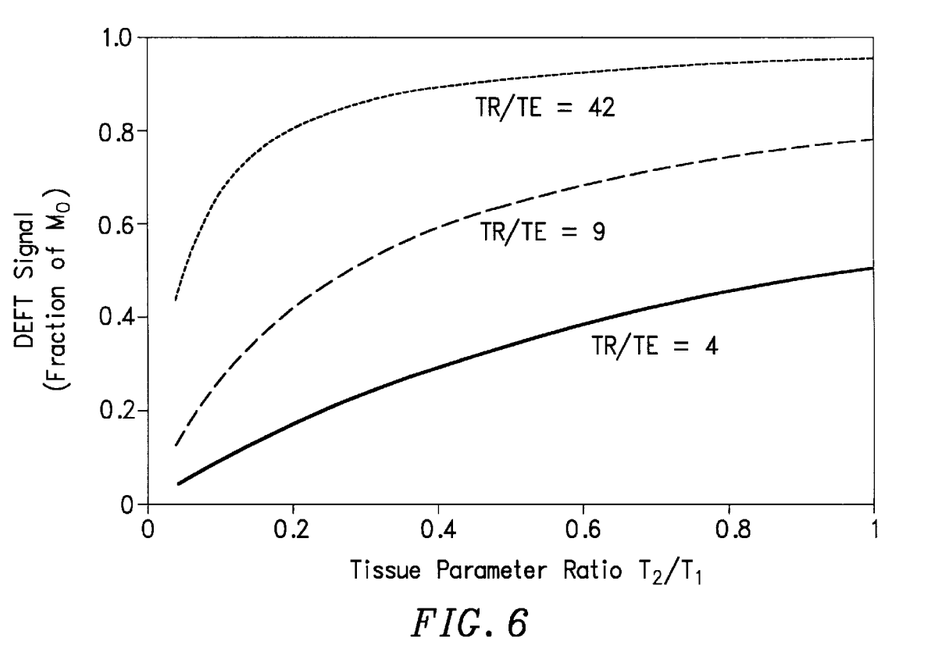
FIG. 6 illustrates a DEFT signal as a function of T1/T2 for different TE/TR. As with other sequences, there is a trade-off between high SNR and high contrast between tissues.

As with most sequences, the scan parameter choice is a tradeoff between SNR efficiency and contrast. FIG. 6 shows the DEFT signal as a function of T2/T1 for the tissue, plotted for different scan parameters. If TR/TE is too high, the SNR will be good, but the contrast may not be good. A lower TR/TE will give better contrast and (usually) a lower scan time, but possibly lower SNR. Note that care should be taken when using FIG. 6 to determine good parameters for tissue contrast because it does not take into account ρ differences. In the case of cartilage and joint fluid, little contrast is necessary from DEFT itself, because the ρ differences alone provide good contrast.

The patellofemoral joint of several volunteers were scanned using T1-weighted SPGR, ρ-weighted FSE and DEFT sequences. The SNR and CNR were measured from one of the images and compared to predicted results using the same parameters as the scans.

All images were acquired on a 1.5 T GE Signa scanner with 22 mT/m, 77 T/m/s gradients. A 3-inch surface coil was placed directly over the patella. The 3-inch diameter coil allows a field-of-view (FOV) of 10 cm and gives a better SNR than the Extremity coil. Other scan parameters are shown in Table 2.

TABLE 2

Scan Parameters Used in Imaging Comparisons

| Quantity | SPGR | FSE | DEFT |
| --- | --- | --- | --- |
| TR(ms) | 50 | 3500 | 400 |
| TF(ms) | 15 | 15 | 15 |
| NEX | 2 | 1 | 2 |
| Echo Train Length | 1 | 4 | 1 |
| Resolution (mm) | 0.4 | 0.4 | 0.4 |
| Scan Time(s) | 50 | 230 | 210 |
| Slice Thickness (mm) | 3 | 3 | 3 |
| Fat Suppression | yes | yes | yes |

Figure 7A:
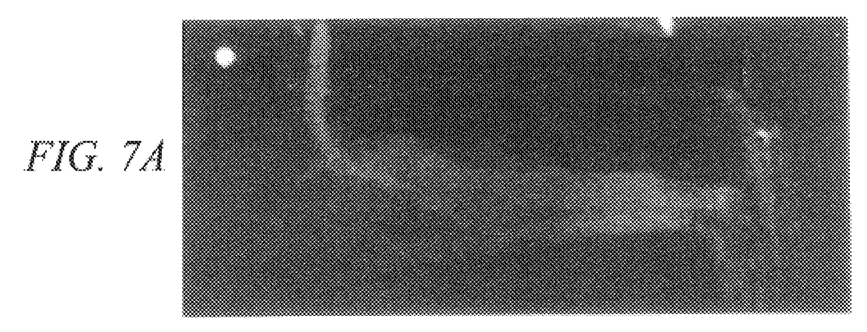
FIGS. 7a–7c illustrate axial images of the patellofemoral joint of a normal volunteer.
Figure 7B:
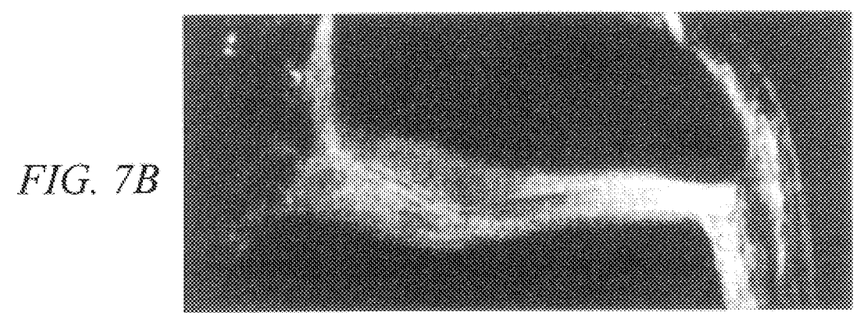
Figure 7C:
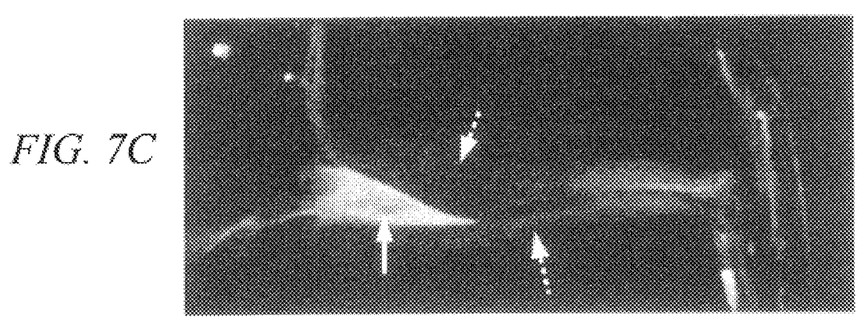

FIG. 7 shows the cartilage in the patellofemoral joint of a normal volunteer. The DEFT image shows very bright synovial fluid (solid arrow) in the joint, combined with clearly depicted cartilage (dotted arrow). Although the FSE image shows bright cartilage, there is slight blurring due to T2-decay in late echoes. Also, the contrast on both FSE and SPGR images is not nearly as high as in the DEFT image.

The images herein are of higher resolution than many images presented, which typically use a FOV of about 15 cm and a 256×256 matrix size. The images have the same matrix size, but over a 10 cm FOV so that the resolution is higher in our images. This resolution difference is equivalent to a loss of a factor of about 2.2, which emphasizes the need for high signal strength to simultaneously achieve good SNR and high resolution.

SNR and CNR values were calculated u sing small region-of-interest measurements on the images. For cartilage signal, five regions were used, and were consistent between the DEFT, FSE and SPGR images. Background noise was calculated using two regions on each image, and the average used as the noise value. For each of the five cartilage signal regions, the SNR was calculated.

The ratio of cartilage SNR on FSE and SPGR images to cartilage SNR on the DEFT image was calculated for each of the five regions. The mean value is reported in Table 3, with an uncertainty equal to half the range of values over the five regions.

TABLE 3

Comparison of Sequences for Cartilage Imaging:
Measured and Predicted SNR and CNR Relative to DEFT.

| Quantity | FSE | SPGR | DEFT |
|---|---|---|---|
| Predicted SNR/SNR$_{DEFT}$ | 1.34 | 0.29 | 1.0 |
| Measured SNR/SNR$_{DEFT}$ | 1.47 ± 0.23 | 0.43 ± 0.08 | 1.0 |
| Predicted CNR/CNR$_{DEFT}$ | 0.1 | 0.08 | 1.0 |
| Measured CNR/CNR$_{DEFT}$ | 0.13 ± 0.5 | 0.23 ± 0.10 | 1.0 |

Theoretical signal and contrast levels were calculated using Eqs. 6 and 7. However, no theoretical noise values are used. instead we assumed the noise is identical on all three sequences, and compared relative quantities. The cartilage SNR and the cartilage-fluid CNR of the three sequences are compared by taking the ratio of each quantity for SPGR or FSE to the corresponding quantity for DEFT. Table 3 shows the measured and predicted SNR and CNR for SPGR and FSE compared to DEFT.

Figure 8A:
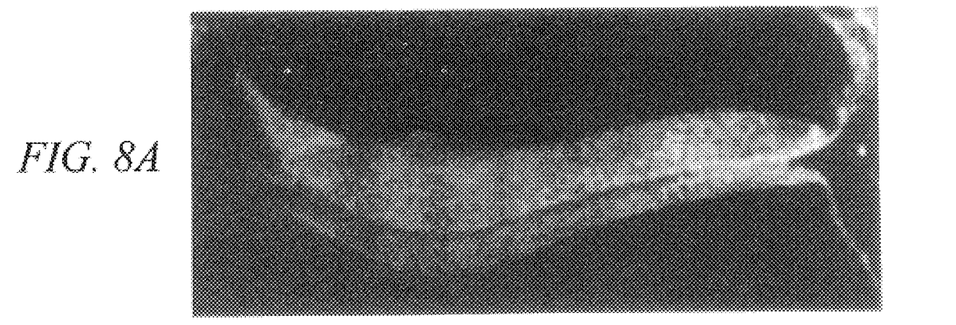
FIGS. 8a–8c illustrate axial images of the patellofemoral joint of a patent with knee pain.
Figure 8B:
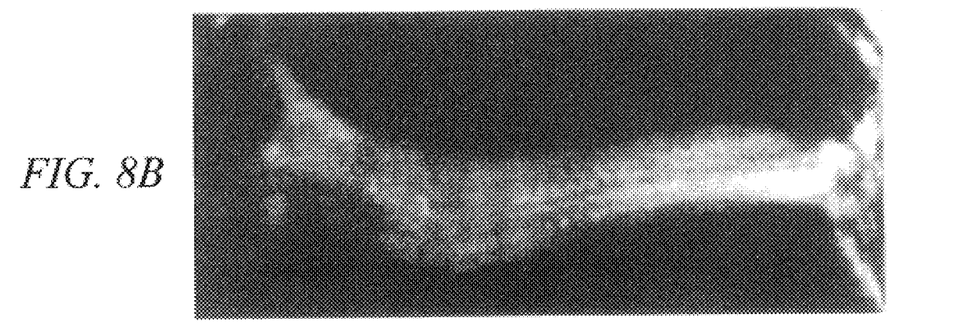
Figure 8C:
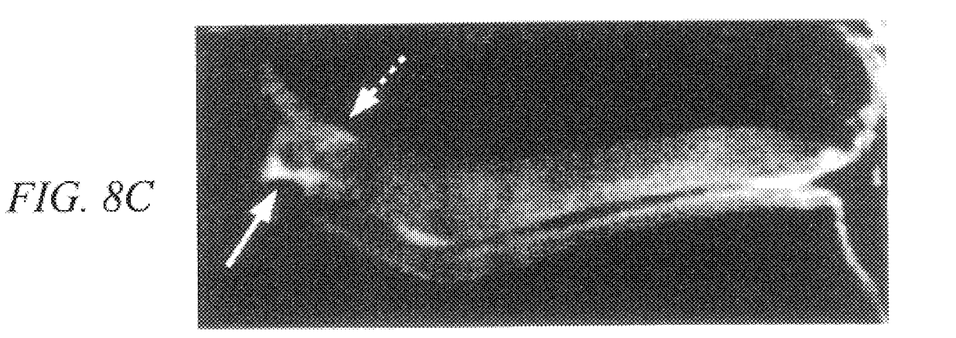

FIG. 8 shows patellar cartilage with an irregular surface and a small cartilage fissure. The cartilage fissure is high in signal intensity on the DEFT image, probably reflecting joint fluid tracking into the fissure. The cartilage fissure and surface irregularity are difficult to see on the SPGR or FSE images, but are very clearly identified on the DEFT image. This is a good illustration of the value of cartilage-fluid contrast in diagnosing cartilage injuries.

DEFT has been used in the past to enhance signal levels, and DEFT images of the knee were recently presented in (30) and in (31), by us. In their work, Oshio et al. (30) compare the fluid enhancement seen on their "Fast-Recovery RARE" sequence to the enhancement in MR arthrography. Their "Fast-Recovery RARE" sequence uses a 3-echo train and a tipup pulse with a longer effective TE than our sequence, resulting in different contrast. The present invention directly approaches the problem of cartilage imaging in that the sequence for cartilage SNR, rather than contrast, is optimized. Both "Fast-Recovery RARE" and Deft images of cartilage demonstrate the strong fluid-cartilage contrast achieved from the strong fluid signal.

The pure "T2/T 1" contrast seen in DEFT imaging is clearly different to either T1-contrast or T2-contrast. In many cases, because the T2/T1 ratio is similar in many soft tissues, DEFT does not result in much contrast. This is the case with gray and white matter in the brain.

In most cases, differences in proton density of different tissues can be neglected. However, in the case of imaging articular cartilage, it is shown that proton density is a significant factor in determining the contrast between cartilage and synovial fluid. It is largely the fact that both the T2 and the proton density of cartilage are lower than those of joint fluid that results in the high fluid-cartilage contrast seen on T2-weighted and DEFT images.

The primary benefit of DEFT, compared to other methods, is that it provides high contrast without loss of cartilage signal. While T2-weighted methods generate contrast by waiting for the signal from the short-T2 species to decay, DEFT produces similar contrast by enhancing the signal of long-T2 species. The SNR efficiency of DEFT for cartilage imaging is comparable to FSE or GRE sequences.

Driven equilibrium methods attempt to recover as much of the magnetization as possible before allowing for T 1 recovery as other sequences do. When compared to spin echo techniques, the only disadvantage of DEFT is that the recovery time is shortened because an additional spin echo is used. However, this is usually insignificant compared to the signal gain from using a tip-up pulse.

The TE and TR parameters used in our imaging sequence give $_{t2}$=30 ms and $_{t1}$=370 ms. This gives a theoretical signal ratio (synovial fluid/cartilage) of 1.62. These parameters were chosen to give a reasonable compromise between scan time and cartilage signal level. A longer TR (or equivalent shorter TE) would give higher signal levels, but slightly lower contrast, as was shown in FIG. 6.

DEFT has been compared to SPGR and FSE sequences with little T2 weighting. T2-weighted sequences increase the contrast between cartilage and joint fluid. However, because the goal was to maximize both contrast and SNR efficiency, we did not use T2-weighted methods.

There is reasonably good agreement about the tissue parameters of cartilage. In several references (12, 19, 27, 28). It is found the T1 values for cartilage measured 1.5 T were 674 ms, 755 ms, and 1089 ms. The T2 values from all references vary from 30 ms to 52 ms. Cartilage T2 is expected to vary across the cartilage itself, as reported in (28).

For synovial fluid, there is considerably less agreement on the tissue parameters. The two T1 values (at 1.5 T) are 1470 ms and 3176 ms. T2 values vary from 177 ms to 800 ms. It is believed that the methods used to obtain the lower T2 values are not as accurate as those used to obtain the longer T2.

Figure 9:
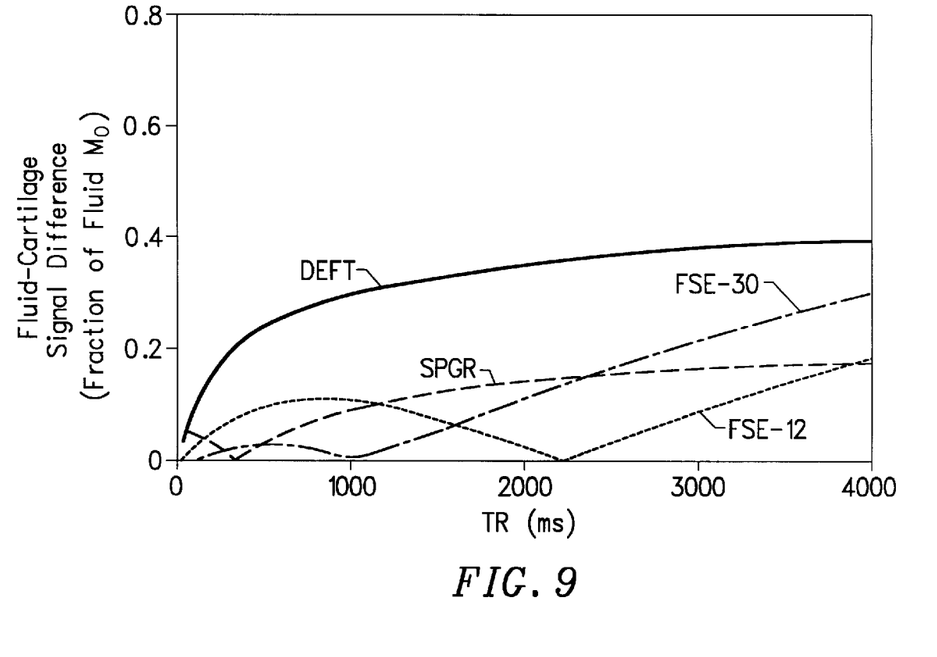
FIG. 9 illustrates a comparison of cartilage—fluid contrast.

The choice of T1 and T2 values can make noticeable differences in the plots. However, the overall conclusion, that DEFT provides the best contrast-SNR trade off of the sequences we compared, remains the same. This is shown in FIG. 9, which repeats FIG. 5 with T1=3000 ms and T2=200 ms for synovial fluid instead of the values in Table 1.

Although MRI is the preferred modality for diagnosing knee abnormalities, current sequences are often limited in their ability to depict abnormal articular cartilage. Typically sequences provide either high contrast between cartilage and surrounding tissue or a high cartilage SNR. It has been shown, both theoretically and experimentally that fat-suppressed DEFT imaging simultaneously provides both tissue contrast and cartilage SNR which are comparable to the best contrast or SNR of other sequences.

DEFT results in a signal level which is a function of the ratio T1/T2. In many clinical applications, this does not provide useful contrast, as many tissues have similar ratios of T1/T2. However, for cartilage and synovial fluid, the combined effect of higher proton density and lower T1/T2 ratio in fluid than cartilage produces excellent contrast. Although this contrast is similar to that of T2-weighted sequences, the signal level of the cartilage itself using DEFT is much higher than that of T2-weighted sequences. When compared to other scan-time efficient methods such as FSE or GRE, the contrast of DEFT is substantially better. Images of the patellofemoral cartilage obtained in 15 volunteers support the predictions of high contrast and SNR of fat-suppressed DEFT imaging.

While the invention has been described with reference to specific embodiments, the description is illustrative of the invention and not limiting the invention. Various modifications and applications may occur to those skilled in the art without departing from the true spirit and scope of the invention as defined by the appended claims.

What is claimed is:

1. A method of imaging a material with improved contrast in a region of an objectxsing magnetic resonance, said material having relaxation times $T_1$ and $T_2$, said method comprising the steps of:

a) placing the object in a static magnetic field along a longitudinal axis (z), b) applying a first slice selective excitation pulse to tip nuclear spins through an angle α about a second axis (x) in a rotating frame (x,y), c) applying a first refocusing pulse along a third axis in the rotating frame (y), d) detecting a first spin echo at a time TE after application of the slice selective pulse, e) applying a second refocusing pulse along the third axis in the rotating frame (y), f) applying a second slice selective excitation pulse through an angle -α about the second axis (x) in the rotating frame at a time TE after detecting the first spin echo for driving any remaining transverse magnetization back to the longitudinal axis, and g) repeating steps b) through f) with step b) repeated at a time $\tau_1$ after applying the second slice selective excitation pulse, time $\tau_1$ being equal to the process repetition rate, TR, minus twice the echo time, TE.

2. The method as defined in claim 1 wherein in steps c) and e) the refocusing pulse comprises a composite of pulses.

3. The method as defined by claim 1 wherein at least two materials are imaged, the materials having different values for $T_1$, $T_2$, and proton density, ρ, and wherein steps b) through f) comprise a driven equilibrium Fourier transform (DEFT) in which a high signal to noise ratio (SNR) and a high contrast to signal ratio (C(R) of the materials are realized in an image.

4. The method as defined in claim 3 wherein the time between steps b) and f) is $\tau_2$, ρ is the proton density of the material, C is the equilibrium magnetization per proton, and $M_{ss}$ is the static magnetic field and $\tau_1$ and $\tau_2$ are chosen such that $$M_{ss} \approx \frac{\rho C}{1 + \frac{T_1}{T_2}\frac{\tau_2}{\tau_1}}$$

5. The method as defined in claim 4 wherein the imaged material includes cartilage.

6. The method as defined in claim 5 wherein the imaged material includes joint fluid.

7. The method as defined in claim 1 wherein the imaged material includes cartilage.

8. The method as defined in claim 7 wherein the imaged material includes joint fluid.

9. A method of imaging with improved contrast a material in a region of an object sing magnetic resonance, said material having relaxation times $T_1$ and $T_2$, said method comprising the steps of:

a) placing the object in a static magnetic field along a longitudinal axis (z), b) detecting a magnetic resonance signal using a pulse echo sequence including a first transverse excitation pulse and a first refocusing pulse to form a pulse echo at an echo time, TE, after applying the first transverse excitation pulse, c) applying a second refocusing pulse, d) applying a second transverse excitation pulse at a time, TE, after detecting the magnetic resonance signal for driving any remaining transverse magnetization back to the longitudinal axis, e) repeating steps b) through d) with the pulse echo sequence beginning at a time $\tau_1$, after applying the second transverse excitation pulse, $\tau_1$ being equal to the process repetition rate, TR, minus twice the echo time, TE.

10. The method as defined in claim 9 wherein in steps b) and c) the refocusing pulse comprises a composite of pulses.

11. The method as defined by claim 9 wherein at least two materials are imaged, the materials having different values for $T_1$, $T_2$, and proton density, ρ, and wherein steps b) through d) comprise a driven equilibrium Fourier transform (DEFT) in which a high signal to noise ratio (SNR) and a high contrast to signal ratio (CNR) of the materials are realized in an image.

12. The method as defined in claim 11 wherein the time between applying the first transverse excitation pulse and the second transverse excitation pulse is $\tau_2$, ρ is the proton density of the material, C is the equilibrium magnetization per proton, and $M_{ss}$ is the static magnetic field and $\tau_1$ and $\tau_2$ are chosen such that $$M_{ss} \approx \frac{\rho C}{1 + \frac{T_1}{T_2}\frac{\tau_2}{\tau_1}}$$

13. The method as defined in claim 12 wherein imaged material includes cartilage.

14. The method as defined in claim 12 wherein imaged material includes joint fluid.

15. The method as defined in claim 9 wherein imaged material includes cartilage.

16. The method as defined in claim 15 wherein imaged material includes joint fluid.

* * * * *